United States Patent
Ben Ayed

(10) Patent No.: US 8,107,920 B2
(45) Date of Patent: *Jan. 31, 2012

(54) EMERGENCY DETECTION AND NOTIFICATION SYSTEM

(76) Inventor: Mourad Ben Ayed, Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/219,681

(22) Filed: Aug. 28, 2011

(65) Prior Publication Data

US 2011/0298613 A1    Dec. 8, 2011

Related U.S. Application Data

(63) Continuation-in-part of application No. 11/204,482, filed on Aug. 17, 2005, now Pat. No. 7,565,132.

(51) Int. Cl.
*H04M 11/04* (2006.01)

(52) U.S. Cl. ................................... 455/404.1

(58) Field of Classification Search ............ 455/404.1
See application file for complete search history.

(56) References Cited

U.S. PATENT DOCUMENTS

| | | | |
|---|---|---|---|
| 6,836,212 B2 | 12/2004 | Sawinski et al. | |
| 6,992,580 B2 | 1/2006 | Kotzin et al. | |
| 7,005,999 B2 | 2/2006 | Salzhauer et al. | |
| 7,221,928 B2 | 5/2007 | Laird et al. | |
| 7,565,132 B2 | 7/2009 | Ayed et al. | |
| 7,664,463 B2 | 2/2010 | Ayed et al. | |
| 7,715,831 B2 | 5/2010 | Wakefield et al. | |
| 2003/0050039 A1* | 3/2003 | Baba et al. | 455/404 |
| 2004/0199056 A1 | 10/2004 | Husemann et al. | |
| 2005/0085257 A1* | 4/2005 | Laird et al. | 455/550.1 |
| 2005/0153680 A1 | 7/2005 | Yoshioka et al. | |
| 2005/0280546 A1 | 12/2005 | Ganley et al. | |

* cited by examiner

*Primary Examiner* — Temesgh Ghebretinsae
*Assistant Examiner* — David Bilodeau
(74) *Attorney, Agent, or Firm* — Daniel Schein, Esq.

(57) ABSTRACT

An emergency detection and notification system containing a short wireless transceiver collects sensor information from onboard sensors and or remote sensors and detects conditions that require attention.

Upon detection of an exception, the emergency detection and notification system issues an audible request, and awaits a confirmation from the user.

If a confirmation is not received, the emergency detection and notification system instructs a remote terminal or a VOIP service to dial a phone number, to issue messages, and to issue vocal signals corresponding to sensor information.

20 Claims, 11 Drawing Sheets

EMERGENCY DETECTION AND NOTIFICATION SYSTEM

PRIORITY

The present application is a Continuation-In-Part ("CIP") of U.S. patent application Ser. No. 11/204/482, now U.S. Pat. No. 7,565,132, filed Aug. 17, 2005.

FIELD OF THE INVENTION

This invention is directed generally to emergency detection and notification systems and more specifically to a portable device that monitors health signs and that automatically calls a phone number or sends an email when it detects a condition that requires medical attention.

BACKGROUND OF THE INVENTION

Existing emergency detection and notification systems comprise a trigger device and a base station connected to a telephone jack that automatically dials an emergency service when a person activates the trigger device. These devices are costly and require a fixed phone line. These devices do not call automatically on detection of a condition that requires attention. Other emergency detection and notification systems use sensors—such as a pulse oximeter—and communicate with a base station using BLUETOOTH. The base station is capable of detecting a health condition and calling a number. This system is cumbersome and not easily portable as it is composed of two parts. Other emergency detection and notification systems use wearable devices to detect emergency conditions, and automatically call support lines. These systems do not interact with the user in a meaningful way, and therefore provide inadequate service and generate frequent false positives.
There is a need for an intelligent emergency detection and notification system that is convenient, portable and reliable.

SUMMARY OF INVENTION

A wearable apparatus comprising: a single short wireless transceiver means wherein said single short wireless transceiver establishes a connection with at least one remote terminal, wherein upon detection of a connection drop, said wearable apparatus can issue an audible alarm;
a memory for storing at least one threshold and, at least one emergency phone number and, at least one emergency message;
a speaker, at least one battery, a means for collecting sensor information, wherein the volume of said wearable apparatus is less than 150 cm3, wherein the emitted energy of said wearable apparatus is less than 100 milliwatts, wherein said wearable apparatus does not include any cellular network transceiver;
wherein upon detection of sensor information not matching said at least one threshold, issuing an audible request through said speaker, waiting for a response selected from the group consisting of: a button push, an voice reply, a motion;
wherein if a valid response is not received within a predetermined period of time, instructing said at least one remote terminal to dial at least one phone number selected from said at least one emergency phone number, wherein upon detection of at a line picked up, sending voice messages corresponding to said at least one emergency message, sending voice corresponding to said sensor information.

A method comprising: using a wearable apparatus, wherein the wearable apparatus has a volumes less than 150 cm3, wherein the wearable apparatus emits less than 100 milliwatts, wherein the wearable apparatus does not include any cellular network transceiver;
updating the wearable apparatus with information selected from the group consisting of: at least one threshold, at least one emergency phone number, at least one emergency message;
configuring the wearable apparatus to connect with at least one remote terminal using a short wireless transceiver, wherein upon detection of a connection drop, the wearable apparatus can issue an audible alarm;
wherein upon detection of sensor output not matching the at least one threshold, issuing an audible request, waiting for a user response selected from the group consisting of: a button push, an oral reply, a motion;
wherein if a response is not received within a predetermined period of time, instructing said at least one remote terminal to dial at least one phone number selected from said at least one emergency phone number, wherein upon detection of at a line picked up, sending voice corresponding to said sensor output to said at least one remote terminal.

A method comprising: using a wearable apparatus, collecting sensor information from sensor means wherein said sensor means are selected from the group consisting of: onboard sensor means, remote wearable sensor means;
wherein the wearable apparatus emits less than 100 milliwatts, wherein the wearable apparatus connects with at least one remote terminal using a short wireless transceiver;
wherein upon detection of a connection drop, the wearable apparatus can issue an audible alarm message;
wherein upon detection of low battery, the wearable apparatus can issue an audible alarm message;
wherein upon detection of sensor information not matching user defined thresholds, issuing an audible request, waiting for a user response selected from the group consisting of: a button push, an oral reply, a motion;
wherein if the user response is not received within a predetermined period of time,
instructing said at least one remote terminal to dial at least one phone number;
wherein upon detection of at a line picked up, sending voice corresponding to said sensor information to at least one remote terminal.

BRIEF DESCRIPTION OF THE DRAWINGS

The present invention with be more clearly understood after reference to the following detailed specifications read in conjunction with the drawings wherein.

DETAILED DESCRIPTION OF THE PREFERRED EMBODIMENTS

Figure 1A:
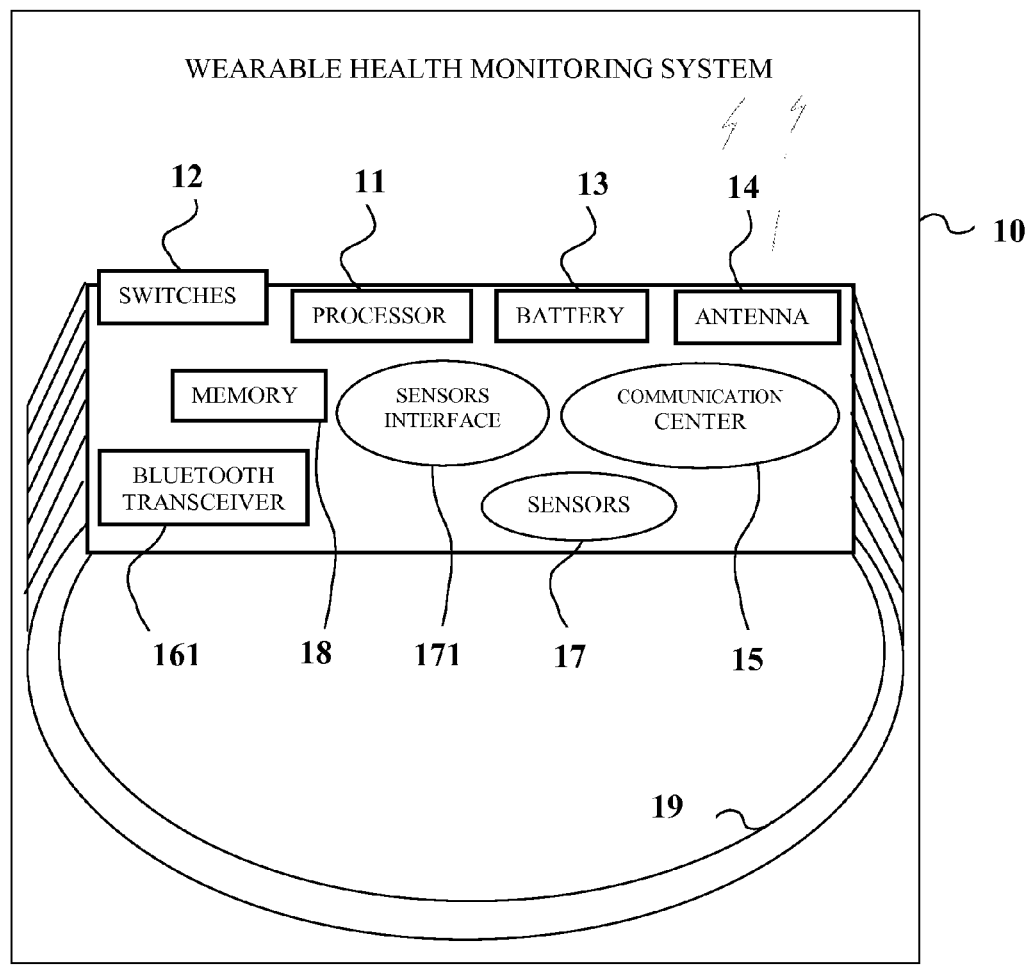
FIG. 1A is a schematic of an emergency detection and notification system

FIG. 1A is schematic of an emergency detection and notification system 10 comprising a processor 11, switches 12, battery 13, antenna 14, communication center 15, BLUETOOTH transceiver 161, sensors 17, sensors interface 171, memory 18 and attachment system 19.

Switches 12 can be any type of buttons, switches, remote sensor switches, touch sensor switches, contact sensor switches, voice activated switches, motion activated switches, remote control activated switches. Switches 12 are used to receive and capture user input after issuing a message through communication center 15.

For example, upon detection of an event, communication center 15 issues an audible message "A chock was detected. Do you want to call for assistance? Yes or No?". The user may answer with a "yes" or "no" command to switches 12, or may press a "yes" switch 12 or a "no" switch 12.

Battery 13 provides power to some of the components of emergency detection and notification system 10. It will be understood that battery 13 may be a fuel cell, nickel-cadmium, lithium, alkaline or nickel-hydride battery or any other portable source of electric power. Battery 13 can also be replaced with photovoltaic cells.

When emergency detection and notification system 10 is not in operation it remains in a dormant state ("sleep-mode") to conserve the energy of battery 13.

Antenna 14 can be any type of antenna including patch antennas and dipole antennas.

Communication center 15 can be any type of visual, audio, tactile or mechanical user interface means capable of conveying information to the user. An example of visual means is an LED, or any visual information display device. Audio means can be any audio device such as a speaker, a buzzer, a Piezo buzzer. Tactile means can be any tactile sensor such as a heat-generating device. An example of a mechanical means is a vibrator.

BLUETOOTH transceiver 161 is any type of short range transceiver or a combination of short range transmitter and short range receiver. In a preferred embodiment, BLUETOOTH transceiver 161 used to communicate with a mobile phone, computer or BLUETOOTH sensors. In case of emergency, emergency detection and notification system 10 commands the mobile phone to dial a phone number through BLUETOOTH Hands Free Profile (HFP).

BLUETOOTH transceiver 161 is a low radiation transceiver with emitted energy of less and 100 milliwatt. In a preferred embodiment, the emitted energy is less than 10 milliwatt. In another preferred embodiment, the emitted energy is less than 1 milliwatt.

BLUETOOTH transceiver 161 can discover other compatible transceivers in the vicinity. BLUETOOTH transceiver 161 can establish a temporary two-way connection or a piconet network with other devices equipped with compatible transceivers.

Sensors 17 can be simple arrangements to collect data such as an infrared detector, a colour detector, a humidity detector, a UV rays detector, a chemical sensor, a NIR sensor.

Sensors 17 can comprise a temperature reader, a blood pressure reader, a heart rate reader, an insulin reader, a prosthesis data reader, a breath analyzer, a scale, a pulse oximeter, a $CO_2$ detector, a carbon monoxide sensor, blood sugar content.

Sensors 17 can comprise a vibration detector, a water detector, an accelerometer, a gyro, a tilt sensor, a motion detector, a microphone.

Sensors 17 can comprise an eye sensor, a cameras, a location sensor, a GPS. In a preferred embodiment, zero or more sensors 17 are onboard the emergency detection and notification system 10.

Sensors interface 171 enables the emergency detection and notification system 10 communicate with remote sensors through BLUETOOTH, WIBREE, ANT, ANT+ or ZIGBEE or any other short wireless low radiation communication protocol.

Zero or more onboard Sensors 17 and zero or more remote sensors generate output signals that are indicative of sensed conditions. Processor 11 compares the output signals to thresholds.

Memory 18 is used for storing at least one threshold and, at least one emergency phone number and, at least one emergency message.

Memory 18 can also store data thresholds such as acceptable temperature, acceptable blood pressure, acceptable heart rate, acceptable insulin level, acceptable pulse, operation hours, operation days, alert messages, recordings, client name, greetings, health conditions, blood type, medications, buzzer type, buzzer volume, buzzer duration, alarm type, and voice messages and recordings.

Memory 18 can be any memory with a size less than 16 Mega bits.

In another embodiment, memory 18 is less than 100 Mega bits.

In another embodiment, memory 18 is less than 1000 Mega bits.

In another preferred embodiment, power consumption is less than 1 mA when the system is in standby.

In another preferred embodiment, power consumption is less than 10 mA when the system is in standby.

In another preferred embodiment, power consumption is less than 100 mA.

Emergency detection and notification system 10 has an attachment system 19 that can be a bracelet, a watch, a pager, a wearable blood pressure monitor, a belt, a device that attaches around the wrist, a device that attaches around the ankle, a device that attaches around the waist, a device that attaches on the chest or any other wearable form. The attachment system may comprise a clip, a ring, a belt, a VELCRO, a keychain, a fastening mechanism or a safety lock to prevent unwanted removal.

In a preferred embodiment, the volume of the emergency detection and notification system is less than 150 cm3, and its weight is less than 100 grams. It comprises one or more short wireless transceivers, and does not comprise any cellular network transceiver.

Figure 1B:
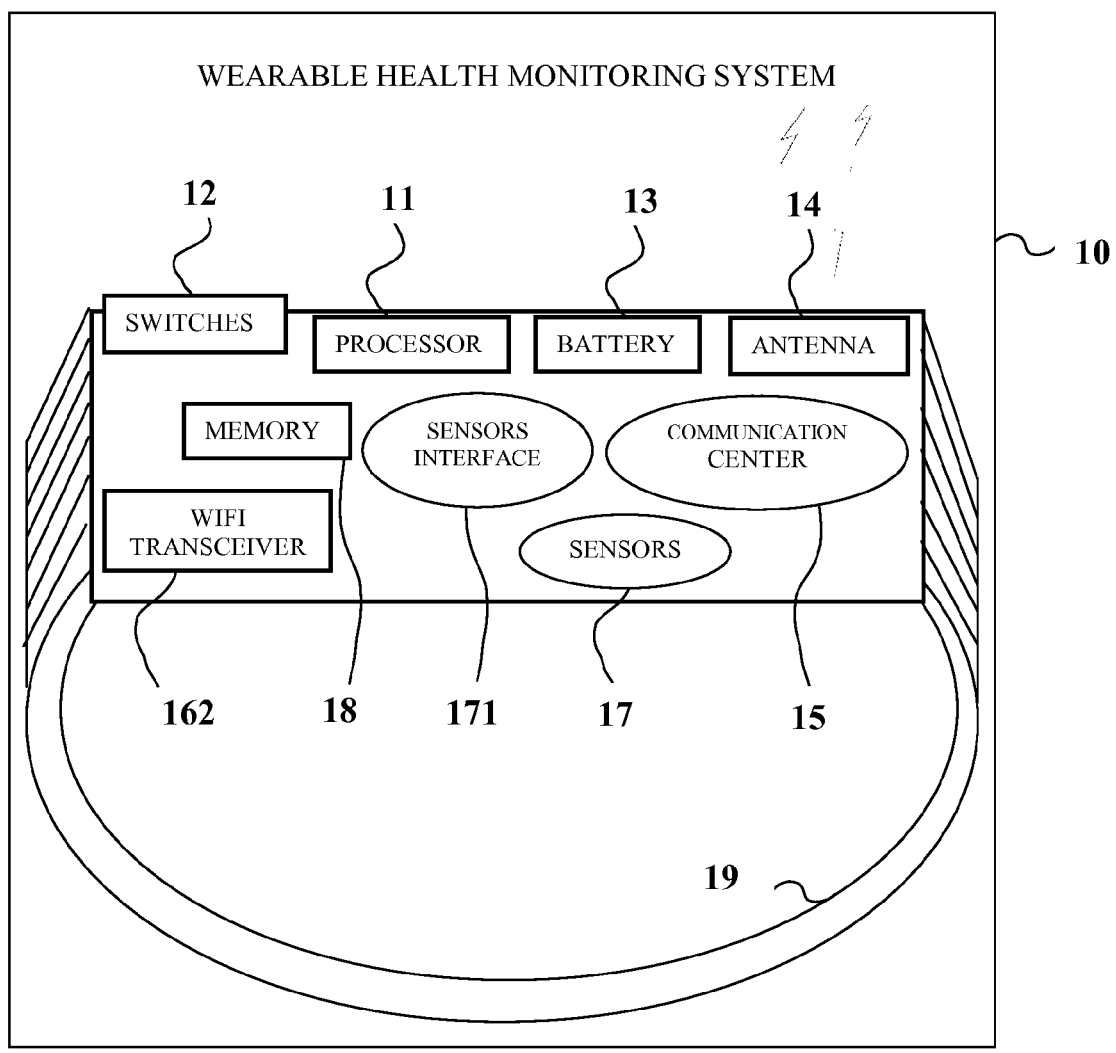
FIG. 1B is an alternative schematic of an emergency detection and notification system

FIG. 1B is schematic of an emergency detection and notification system 10 comprising a processor 11, switches 12, battery 13, antenna 14, communication center 15, WIFI transceiver 162, sensors 17, sensors interface 171, memory 18 and attachment system 19.

In another preferred embodiment, WIFI transceiver 162 allows to connect to an access point and to send commands to a VOIP server to dial a phone number.

WIFI transceiver 162 is a low radiation transceiver with emitted energy of less and 100 milliwatt. In a preferred embodiment, the emitted energy is less than 10 milliwatt.

WIFI transceiver 162 can discover other compatible transceivers in the vicinity and establish a temporary two-way connection with other devices equipped with compatible transceivers.

Figure 2A:
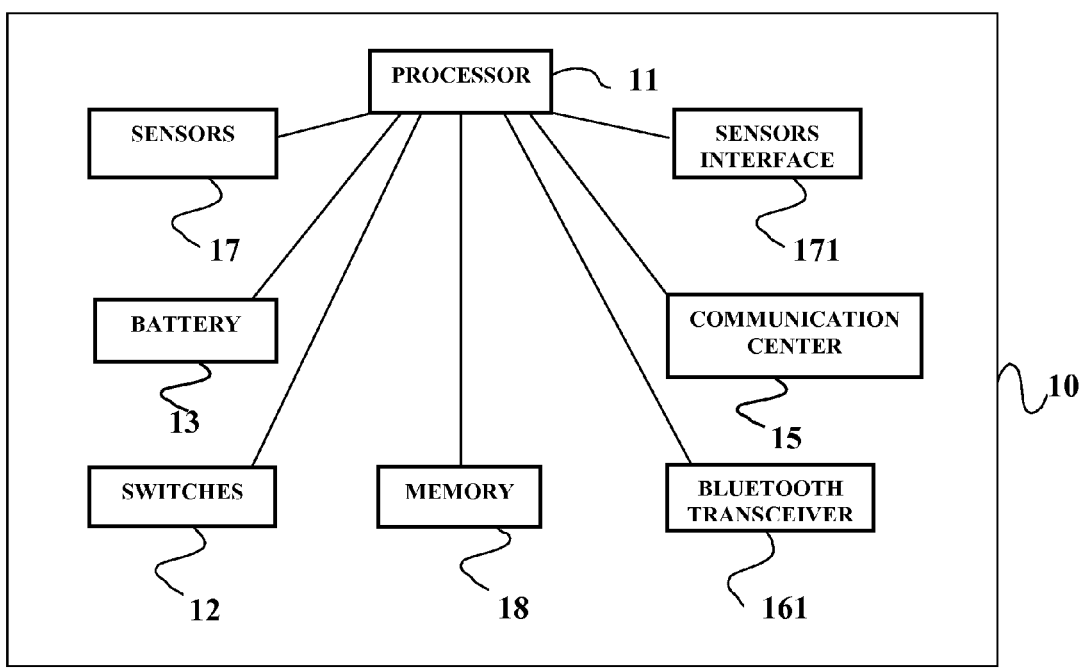
FIG. 2A is a block diagram of an emergency detection and notification system

Referring now to FIG. 2A, in one embodiment, emergency detection and notification system 10 comprises a processor 11 interconnected with switches 12, battery 13, communication center 15, BLUETOOTH transceiver 161, sensors 17, sensors interface 171, and memory 18.

Figure 2B:
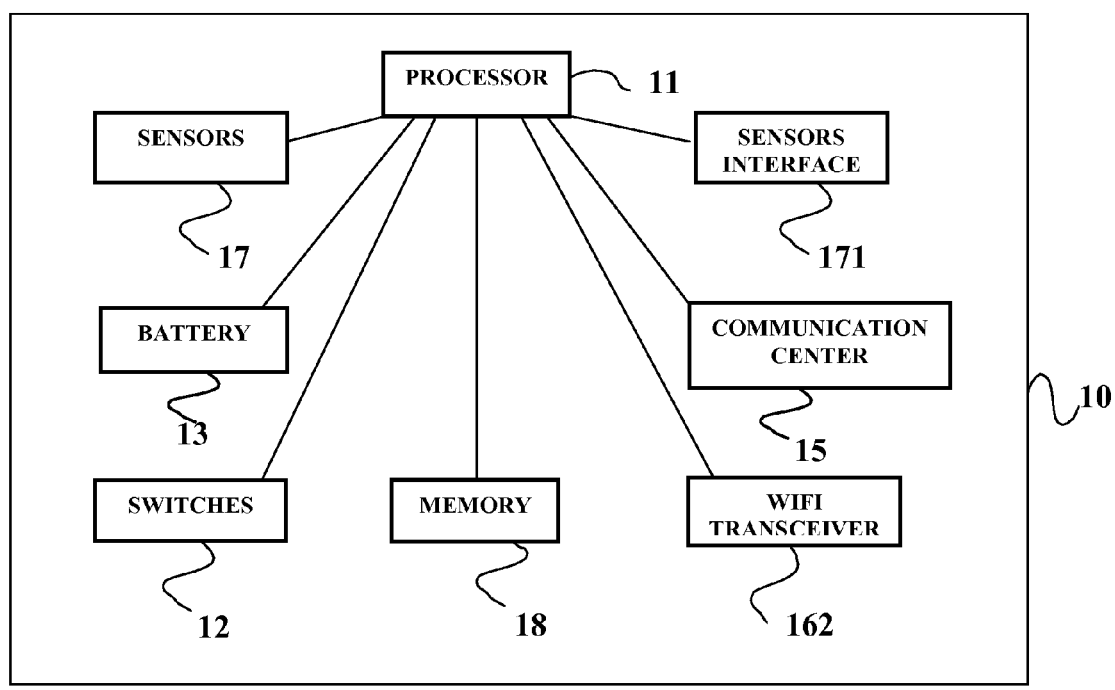
FIG. 2B is an alternative block diagram of an emergency detection and notification system

Referring now to FIG. 2B, in one embodiment, emergency detection and notification system 10 comprises a processor 11 interconnected with switches 12, battery 13, communication center 15, WIFI transceiver 162, sensors 17, sensors interface 171, and memory 18.

Figure 3:
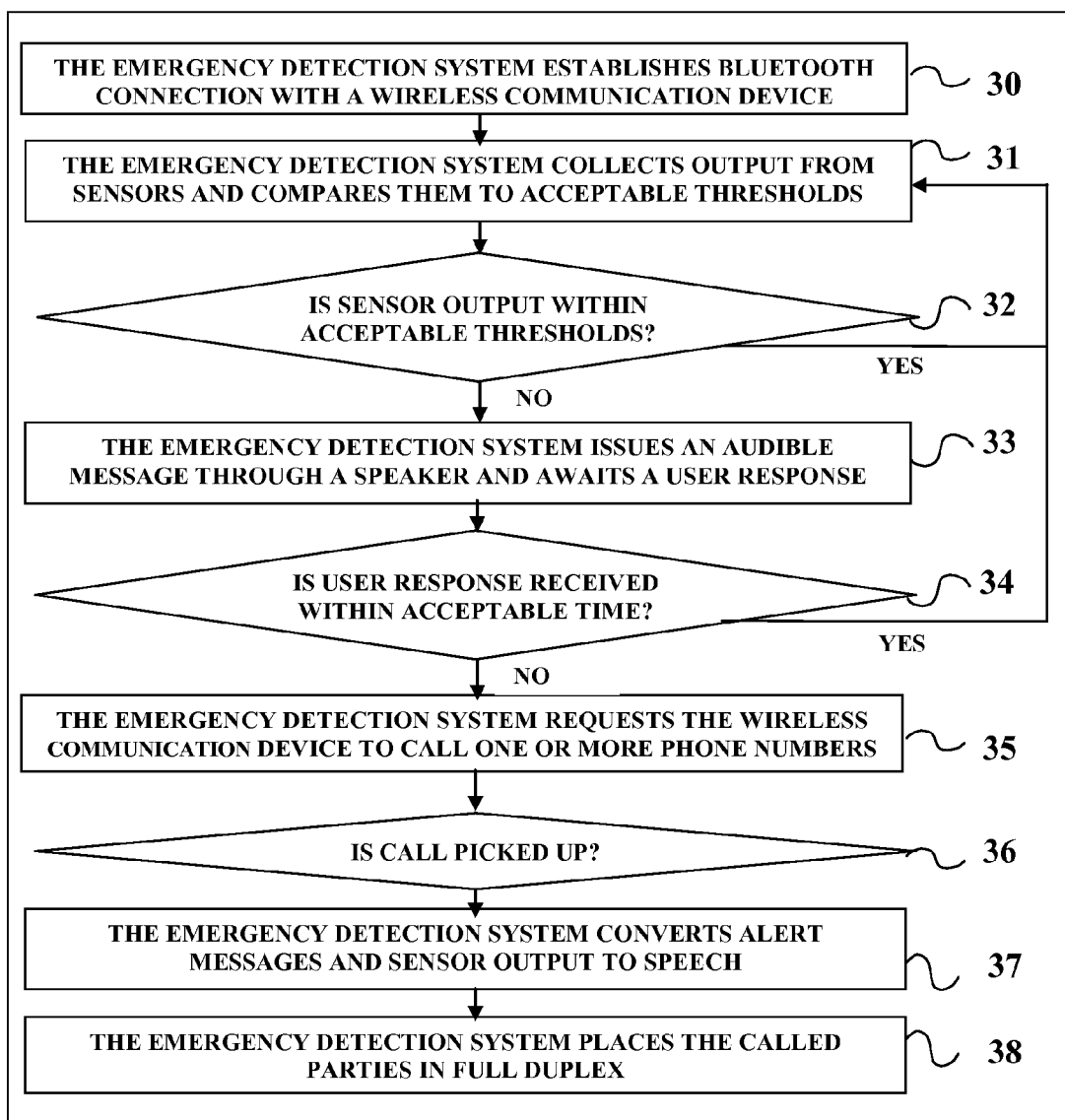
FIG. 3 is a flowchart illustrating the operation of an emergency detection and notification system using BLUETOOTH

Turning now to FIG. 3, the flowchart illustrates the operation of an emergency detection and notification system 10 using BLUETOOTH. In step 30 the emergency detection and notification system establishes a BLUETOOTH connection with a wireless communication device. The emergency detection and notification system is previously paired with the wireless communication device, and the PIN codes are previously entered (if needed). If a connection cannot be established, communication center 15 issues an audible alarm message. Audible alarm message can be a buzzer, a ring, or a voice message.

In step 31, sensors 17 collect sensor data from onboard sensors and remote wireless sensors and compare their outputs to user defined acceptable thresholds. The user defined acceptable thresholds are programmed by the user through a computer connected through a cable, an onboard keypad, a BLUETOOTH paired mobile phone, or a connected WIFI terminal.

In step 32, if sensor output is found outside the acceptable thresholds, an alarm condition is identified and the emergency detection and notification system 10 issues an audible request to the user through communication center 15 and waits for a user response for a predetermined period of time in step 33. For example, it may issue the following message:

"A chock was detected. Do you want to call for assistance? Yes or No?"

"A health condition was detected. Do you want to call for assistance? Yes or No?"

In an alternative embodiment, the emergency detection and notification system 10 issues a vibration or a visual indication to the user and waits for a response. In step 34, if a user response is not received within a predetermined period of time, it is assumed that the user is out of conscience.

In a preferred embodiment, a user response is a voice response. In another embodiment, the user response is a motion response such as pushing a button or waiving a hand. The emergency detection and notification system 10 will command the connected mobile phone to call one or more emergency phone numbers stored in memory in step 35. The wireless communication device dials and establishes a cellular network communication with at least another communication device based on user parameters and user rules.

When a called line is picked up in step 36, the emergency detection and notification system 10 converts text messages, user messages and sensor output to speech in step 37 using text to speech conversion means such as a voice synthesizer. For example, the emergency detection and notification system 10 can get GPS data from a GPS sensor, and convert it to speech: "the user position is Latitude is thirty eight degrees fifty minutes twenty two point zero eight three seven seven seconds north . . . " corresponding to GPS reading of 38°53'22.08377"N . . . .

In another example, the emergency detection and notification system 10 says the name of the patient, the emergency condition, the state, and the sensor readings, "Mrs. Johnson has fallen. She is not responding to questions. The heart beat is one hundred . . . ."

The emergency detection and notification system 10 can also play some pre-recorded recordings.

The emergency detection and notification system 10 plays the function of a life monitor as it can detect if the user is out of conscience (for example is user got into an accident and is not responding, or if user got a heart attack and is not responding, or if the user had an epileptic seizure and is not responding, etc. . . . ), and can ensure that it automatically calls for help and provides assistance. Furthermore, the emergency detection and notification system 10 plays a health monitor function as it can monitor multiple health signs, and can inform the user and call for help should a health condition arise.

In step 38, the emergency detection and notification system 10 opens a full duplex between the user and the called party so that the called party can hear the user and can talk to him and help him.

In another embodiment, one channel is used for listening to the user.

On top of a voice message, the emergency detection and notification system 10 can also send text messages (SMS or email) to the called party containing sensor data. The voice and/or text messages may contain prerecord messages, data, data converted to voice through a synthesizer, or any combination of the above.

In another embodiment, the user responds to the message from the emergency detection and notification system 10 by issuing a voice response. The emergency detection and notification system 10 interprets the voice response and compares it to acceptable responses. The emergency detection and notification system 10 may do voice recognition. If the response is not understood or is not valid, the emergency detection and notification system 10 commands the connected phone to call one or more emergency phone numbers stored in memory.

If a response is understood or is valid, the emergency detection and notification system 10 performs actions according to pre-configured business rules.

In another embodiment, the user responds to the message from the emergency detection and notification system 10 by pressing one or more buttons. The emergency detection and notification system 10 interprets the buttons push and compares it to acceptable responses. If the response does not match with acceptable responses or is not valid, the emergency detection and notification system 10 commands the connected phone to call one or more emergency phone numbers stored in memory.

If a response is accepted, the emergency detection and notification system 10 performs actions according to pre-configured business rules.

In a preferred embodiment, the emergency detection and notification system 10 or the VOIP server generates electrical signals corresponding to sensor output or part of sensor output, and producing sounds on a remote terminal.

In a configuration step, the user defines what phone numbers to dial or SMS or what email addresses to email. The user also defines the rules and conditions under which those numbers/emails are dialed/emailed and what messages are sent. When those conditions occur, those phone numbers are emailed and those SMS/emails are sent.

Figure 4:
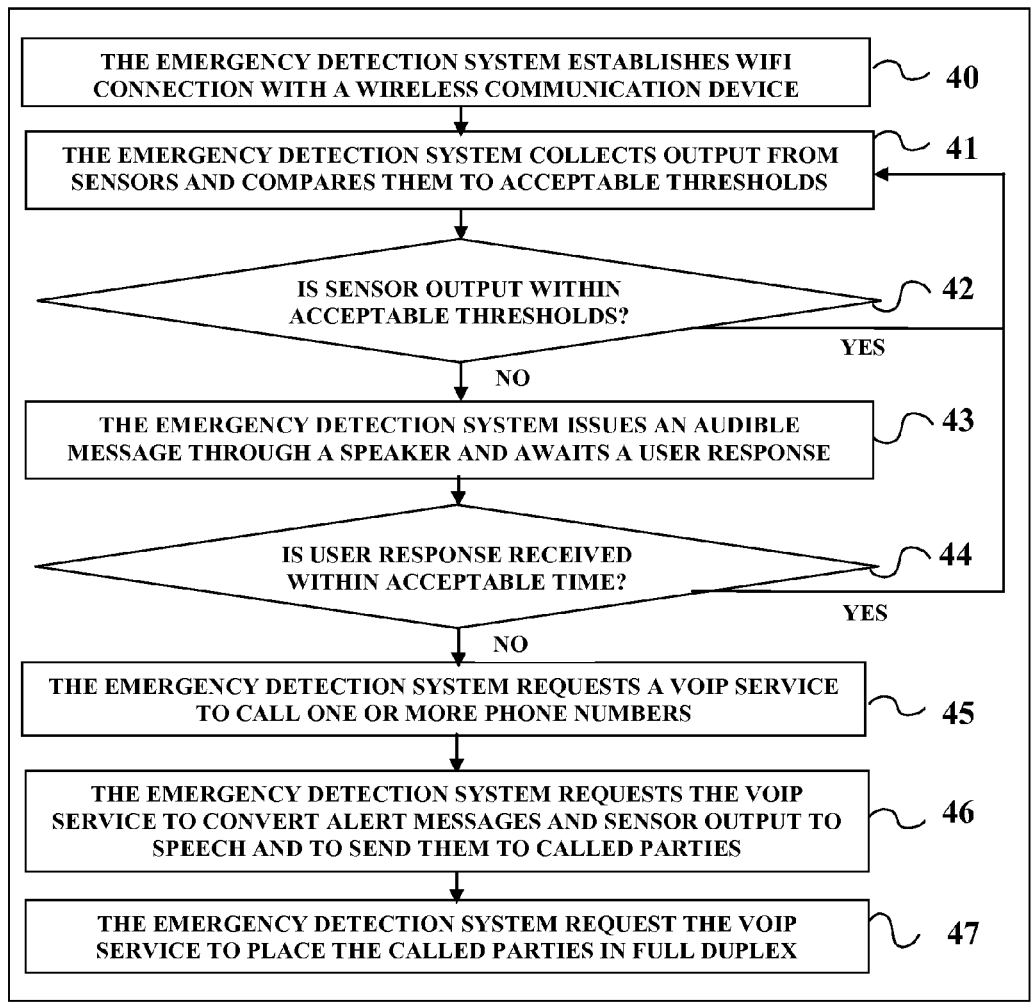
FIG. 4 is a flowchart illustrating the operation of an emergency detection and notification system using VOIP

Turning now to FIG. 4, the flowchart illustrates the operation of an emergency detection and notification system using VOIP.

In step 40 the emergency detection and notification system establishes a WIFI connection with a wireless communication device. The emergency detection and notification system is previously connected with the wireless communication device and the security keys are previously entered (if needed).

In a preferred embodiment, the emergency detection and notification system establishes a connection with a VOIP service. A VOIP service can be SKYPE service, OOVOO service, GOOGLE TALK service, or any other service capable of dialing a number and establishing a voice channel between a user using a wearable device and a dialed number.

In a preferred embodiment, the voice channel is a two way voice channel.

If a connection cannot be established, communication center 15 issues alarms.

In step 41, sensors 17 collect sensor data from onboard sensors and remote wireless sensors and compare their outputs to user defined acceptable thresholds. The user defined acceptable thresholds are programmed by the user through a computer connected through a cable, an onboard keypad, a BLUETOOTH paired mobile phone, or a connected WIFI terminal.

In step 42, if sensor output is found outside the acceptable thresholds, the emergency detection and notification system 10 issues an audible message to the user through communication center 15 and waits for a user response for a predetermined period of time.

If a user response is not received within a predetermined period of time, it is assumed that the user is out of conscience. The emergency detection and notification system 10 will command the VOIP service to call one or more emergency phone numbers stored in memory in step 45. The VOIP service dials and establishes a network communication with at least another communication device based on user parameters and user rules.

When a called line is picked up in step 46, the emergency detection and notification system 10 converts text messages and sensor output to speech in step 47.

The emergency detection and notification system 10 can also play some pre-recorded recordings.

In step 48, the emergency detection and notification system 10 opens a full duplex between the user and the called party so that the called party can hear the user, can talk to him and help him.

On top of a voice message, the emergency detection and notification system 10 can also send text messages (SMS or email) to the called party containing sensor data. The voice and/or text messages may contain prerecord messages, data, data converted to voice through a synthesizer, or any combination of the above.

Figure 5:
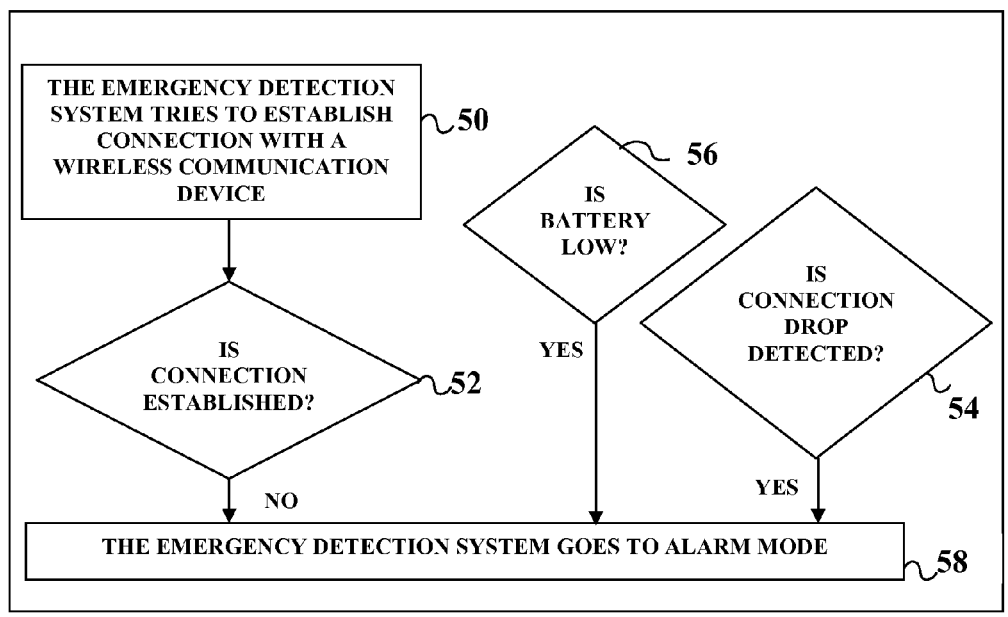
FIG. 5 is a flowchart illustrating initiating the alarming function of the emergency detection and notification system

Turning now to FIG. 5, the flowchart illustrates initiating the alarming function of the emergency detection and notification system.

In step 50, the emergency detection and notification system 10 tries to establish connection with a wireless communication device.

In a preferred embodiment, the connection is BLUETOOTH and the wireless communication device is a mobile phone.

In another embodiment, the connection is WIFI and the wireless communication device is a WIFI terminal.

The emergency detection and notification system 10 establishes a connection with a mobile phone or a VOIP service when it turns ON. The connection must be up at all times in order to guarantee that the emergency detection and notification system 10 is capable of calling a remote number should an alarm condition arise. In step 52, if a connection is not established, the emergency detection and notification system 10 goes to alarm mode in step 58.

In step 54, if the emergency detection and notification system 10 detects a connection failure such as a drop, a disconnect, or a failure to connect, it goes to alarm mode in step 58.

In step 56, if battery is low, the emergency detection and notification system 10 goes to alarm mode in step 58.

In step 58 alarm mode, the emergency detection and notification system 10 can issue vocal alarms as well as visual alarms and mechanical alarms.

An example of a vocal alarm is:

"Cannot connect to mobile phone—System cannot make calls"

"Cannot connect to WIFI—System cannot make calls"

"Battery is low—Please charge"

An example of visual alarm is LED or LED or OLED messaging.

An example of mechanical alarm is vibrator.

Figure 6:
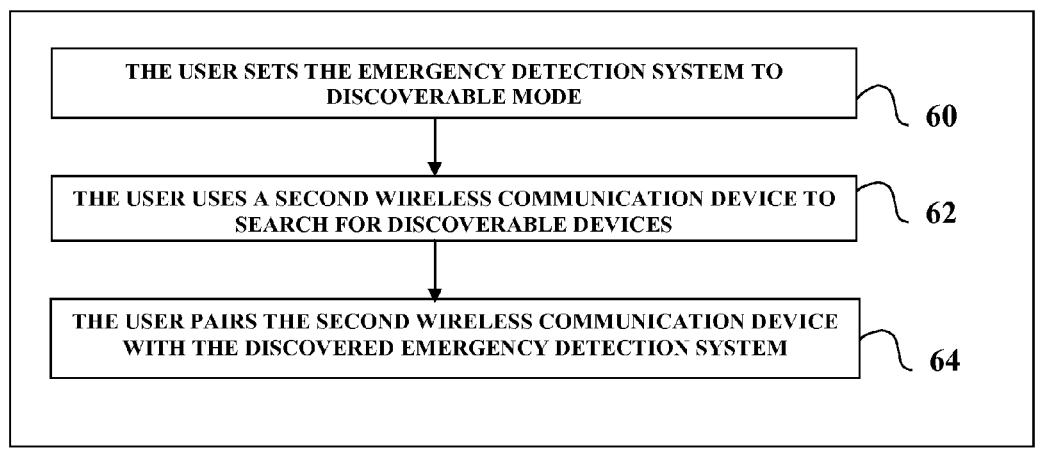
FIG. 6 is a flowchart illustrating pairing the emergency detection and notification system

Turning now to FIG. 6, the flowchart illustrates pairing the emergency detection and notification system with a second device.

In step 60, the user sets the emergency detection and notification system 10 to discoverable mode. This can be done by pressing one or more buttons for a predetermined period of time, by issuing a voice command, or by programming the emergency detection and notification system using a programming cable.

In step 62, the user uses a second device equipped with BLUETOOTH, searches for compatible devices within proximity that are discoverable.

In step 64, the user can select an emergency detection and notification system 10 among the discovered devices for pairing.

The second device may request the user to enter a pairing PIN code which it will authenticate.

Once paired, the emergency detection and notification system 10 becomes non-discoverable. This provides security to the user as the terminal is not visible to other terminals.

Once paired, the emergency detection and notification system 10 can command the second wireless communication device to dial a number, to open voice lines, to relay a message, to play a recording, to issue speech, to receive speech, to hang up, etc.

In another preferred embodiment, the user connects the emergency detection and notification system 10 to a WIFI access point. The emergency detection and notification system 10 may send an authorization code to the WIFI access point for connection the very first time. After that, the emergency detection and notification system 10 can connect to the WIFI access point without entering an authorization code.

Once connected to a WIFI access point, the emergency detection and notification system 10 connects to a VOIP service such as SKYPE service, OOVOO service, GOOGLE TALK service, or any other service capable of dialing a number and establishing a voice channel between a user using a wearable device and a dialed number.

Once connected to a VOIP service, the emergency detection and notification system 10 can command the VOIP service to dial a number, to open voice lines, to relay a message, to play a recording, to issue speech, to convert text to speech, to convert a message to speech, to convert sensor output to speech, to receive speech, to hang up, to convert a text message to speech, etc.

Figure 7:
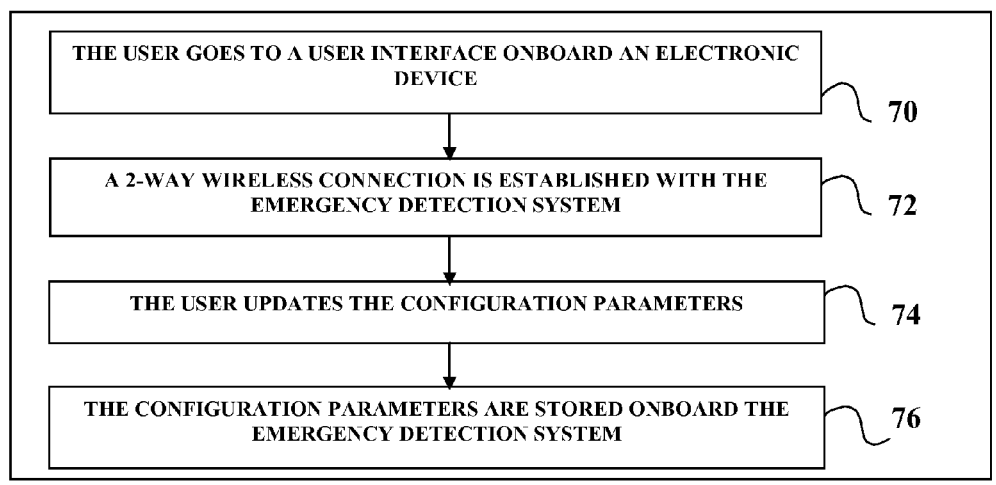
FIG. 7 is a flowchart illustrating configuring the emergency detection and notification system wirelessly

Turning now to FIG. 7, the flowchart illustrates configuring the emergency detection and notification system wirelessly.
In step 70, the user goes to a user interface onboard an electronic device such as a mobile phone, a computer or an electronic device equipped with BLUETOOTH.
In step 72, a two-way wireless connection is established between the emergency detection and notification system 10 and the electronic device.
In step 74, the user enters configuration parameters and files in the user interface and commands the user interface to update the emergency detection and notification system 10.
In step 76, the configuration parameters are stored onboard the emergency detection and notification system 10.

Figure 8:
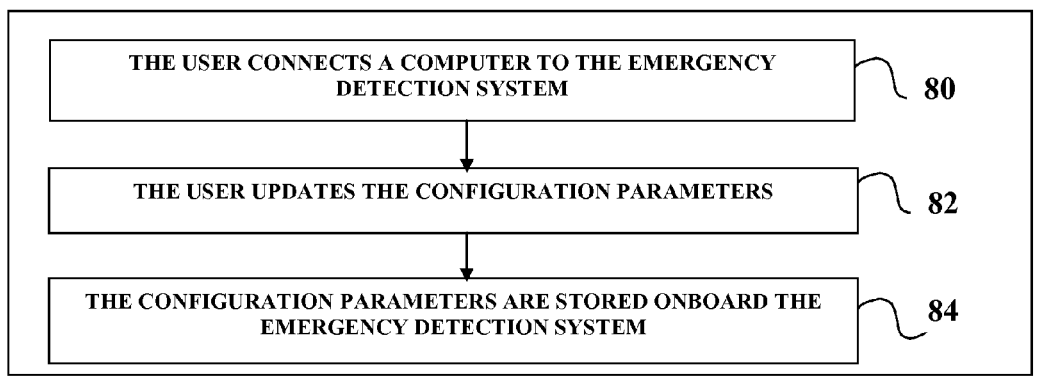
FIG. 8 is a flowchart illustrating configuring the emergency detection and notification system through USB

Turning now to FIG. 8, the flowchart illustrates configuring the emergency detection and notification system through USB.
In step 80, the user connects the emergency detection and notification system 10 to an electronic device such as a mobile phone, a computer or an electronic device equipped with USB.
In step 82, the user enters configuration parameters and files in the user interface and commands the user interface to update the emergency detection and notification system 10.
The user interface allows the user to set configuration parameters or to change them. It may also display old configuration parameters.
Configuration parameters may include data thresholds such as acceptable temperature, acceptable blood pressure, acceptable heart rate, acceptable insulin level, acceptable pulse, operation hours, operation days, alert messages, recordings, client name, greetings, health conditions, blood type, medications, buzzer type, buzzer volume, buzzer duration, alarm type. The configuration parameters are stored onboard the emergency detection and notification system. The user interface program can be installed onboard the portable electronic device from the emergency detection and notification system 10, from a CD, or from other medium such as Internet.
In step 84, the configuration parameters are stored onboard the emergency detection and notification system 10.

Figure 9:
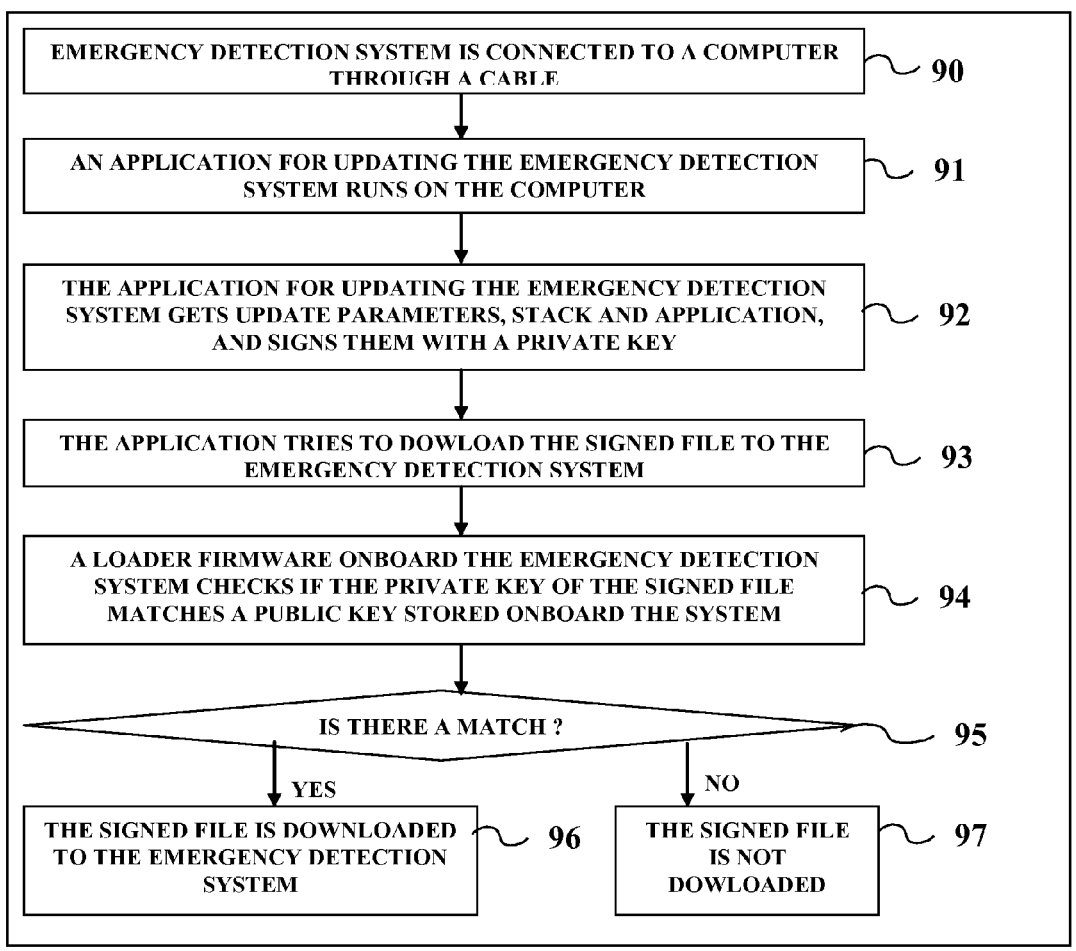
FIG. 9 is a flowchart illustrating updating the emergency detection and notification system Similar reference numerals are used in different figures to denote similar components.

Turning to FIG. 9, the flowchart illustrates updating the emergency detection and notification system 10.
In step 90, the emergency detection and notification system 10 is connected to a computer through a cable. This can be a USB, RS232 or any other cable means. In step 91, the user runs an application to update the emergency detection and notification system 10. The application can be a program running on the computer, a web service, a web plug-in, or any software running on a specialized device.
In step 92, the application collects update parameters, stack and application, and prepares update files. In a preferred embodiment, the application builds a DFU (device firmware upgrade) file. The application can sign the update files using a private key matching a public key stored on the emergency detection and notification system 10.
In step 93, the application tries to download the signed file to the emergency detection and notification system 10.
In step 94, a resident loader firmware onboard the emergency detection and notification system 10 checks if the private key of the signed file matches a public key stored onboard the system or device.
In step 95, if there is a match, the signed file is downloaded to the emergency detection and notification system 10 in step 96. When the new firmware executes, it may set the emergency detection and notification system 10 to discoverable to enable pairing with a new second device.
In step 97, the signed file is not downloaded.
It is noted that the loader firmware cannot be updated through the data port or through the cable. It can only be updated through access to PCB pins or PCB test points, such as SPI pins. This is so that the firmware onboard the emergency detection and notification system 10 cannot be tempered.

Numerous other modifications, variations, and adaptations may be made to the particular embodiment of the invention described above without departing from the scope of the invention, which is defined in the claims. Hence, while exemplary embodiments of the present invention have been set forth above, it is to be understood that the pioneer inventions disclosed herein may be constructed or used otherwise than as specifically described.

The invention claimed is:
1. A wearable apparatus comprising:
  a single short wireless transceiver means wherein said single short wireless transceiver establishes a connection with at least one remote terminal,
    wherein upon detection of a connection failure,
      said wearable apparatus can issue an audible alarm;
  a memory for storing
    at least one threshold and,
    at least one emergency phone number and,
    at least one emergency message;
  a speaker,
  at least one battery,
  a means for collecting sensor information,
  wherein the volume of said wearable apparatus is less than 150 cm3,
  wherein the emitted energy of said wearable apparatus is less than 100 milliwatts,
  wherein said wearable apparatus does not include any cellular network transceiver;
  wherein upon detection of sensor information not matching said at least one threshold,
    issuing an audible request through said speaker,
    waiting for a response selected from the group consisting of:
      a button push, an voice reply, a motion;
    wherein if a valid response is not received within a predetermined period of time,
      instructing said at least one remote terminal to dial at least one phone number selected from said at least one emergency phone number,
      detecting a line picked up,
      sending voice corresponding to said sensor information.

2. The wearable apparatus of claim 1 wherein said means for collecting sensor information is selected from the group consisting of:
  an infrared detector, a colour detector, a humidity detector, a UV rays detector, a chemical sensor, a NIR sensor;
  a temperature reader, a blood pressure reader, a heart rate reader, an insulin reader, a prosthesis data reader, a breath analyzer, a scale, a pulse oximeter, a $CO_2$ detector, a carbon monoxide sensor, blood sugar content;
  a vibration detector, a water detector, an accelerometer, a gyro, a tilt sensor, a motion detector, a microphone;
  an eye sensor, a cameras, a location sensor, a GPS.

3. The wearable apparatus of claim 1 comprising a short wireless low emission transceiver means for communicating with at least one remote wearable sensor and for collecting sensor information wirelessly.

4. The wearable apparatus of claim 1 comprising an attachment means selected from the group consisting of: a clip, a ring, a fastening mechanism, a belt, a Velcro, a keychain.

5. The wearable apparatus of claim 1 having a form selected from the group consisting of:
a bracelet, a watch, a pager, a wearable blood pressure monitor, a belt, a device that attaches around the wrist, a device that attaches around the ankle, a device that attaches around the waist, a device that attaches on the chest.

6. The wearable apparatus of claim 1 comprising a text to speech conversion means wherein said text to speech conversion means generates voice signals.

7. A method comprising:
using a wearable apparatus,
wherein the wearable apparatus has a volumes less than 150 cm3,
wherein the wearable apparatus emits less than 100 milliwatts,
wherein the wearable apparatus does not include any cellular network transceiver;
configuring the wearable apparatus with information selected from the group consisting of:
at least one threshold,
at least one emergency phone number,
at least one emergency message;
configuring the wearable apparatus to connect with at least one remote terminal using a short wireless transceiver,
wherein upon detection of a connection failure,
the wearable apparatus can issue an audible alarm;
wherein upon detection of sensor output not matching the at least one threshold,
issuing an audible request,
waiting for a user response selected from the group consisting of:
a button push, an oral reply, a motion;
wherein if a response is not received within a predetermined period of time,
instructing said at least one remote terminal to dial at least one phone number selected from said at least one emergency phone number,
wherein upon detection of a line picked up,
sending voice corresponding to said sensor output to said at least one remote terminal.

8. The method of claim 7 comprising opening a two way voice channel between said wearable apparatus and said at least one remote terminal.

9. The method of claim 7 wherein
wherein said wearable apparatus instructs said at least one remote terminal to dial a phone number using BLUETOOTH Hands Free Profile.

10. The method of claim 7 comprising
generating electrical signals corresponding to at least one part of said sensor output, and sending said electrical signal to said at least one remote terminal,
wherein said electrical signals produce sounds on said at least one remote terminal.

11. The method of claim 7 comprising
sending at least one message selected from said at least one emergency message to a VOIP server,
instructing said VOIP server to dial said at least one emergency phone number,
instructing said VOIP server to convert said at least one emergency message to speech and to send it to said at least one remote terminal.

12. The method of claim 7 comprising
sending at least one part of said sensor output to said VOIP server,
instructing said VOIP server to convert said at least one part of said sensor output to speech and to send it to said at least one remote terminal.

13. The method of claim 7 comprising
using a user interface to set configuration parameters on the wearable apparatus through means selected from the group consisting of:
a wireless BLUETOOTH connection, a USB cable,
wherein said user interface is selected from the group consisting of:
a mobile application, a computer application, a web site interface, a device interface.

14. The method of claim 7 wherein said configuration parameters comprise parameters selected from the group consisting of:
thresholds, messages, phone numbers,
client name, client information, blood type, health conditions,
operation hours, operation days, language,
buzzer type, buzzer volume, buzzer duration, alarm type.

15. A method comprising:
using a wearable apparatus,
collecting sensor information from sensor means,
wherein said sensor means are selected from the group consisting of:
onboard sensor means, remote wearable sensor means;
wherein the wearable apparatus connects with at least one remote terminal using a short wireless transceiver;
wherein the short wireless transceiver emits less than 100 milliwatts,
wherein upon detection of a connection drop,
the wearable apparatus can issue an audible alarm message;
wherein upon detection of sensor information not matching user defined thresholds,
issuing an audible request,
waiting for a user response selected from the group consisting of:
a button push, an oral reply, a motion;
wherein if the user response is not received within a predetermined period of time,
instructing said at least one remote terminal to dial at least one phone number;
detecting of a line picked up,
sending voice corresponding to said sensor information to at least one remote terminal.

16. The method of claim 15 wherein:
after detection of a line picked up, playing at least one user message.

17. The method of claim 15 wherein:
after detection of a line picked up, opening a two way voice channel between the wearable apparatus and the at least one remote terminal.

18. The method of claim 15 comprising:
connecting to at least one remote terminal using BLUETOOTH Hands Free Profile,
instructing said at least one mobile phone to dial a phone.

19. The method of claim 15 comprising:
generating electrical signals corresponding to sensor information, and sending said electrical signals to said at least one remote terminal,
wherein said electrical signals produce sounds on said at least one remote terminal.

20. The method of claim 15 wherein said remote terminal is a VOIP server.

* * * * *